(12) United States Patent
Yang et al.

(10) Patent No.: US 10,473,693 B2
(45) Date of Patent: Nov. 12, 2019

(54) METHOD AND APPARATUS FOR INFRARED SCANNING NEAR-FIELD OPTICAL MICROSCOPY BASED ON PHOTOTHERMAL EFFECT

(71) Applicant: Bruker Nano, Inc., Santa Barbara, CA (US)

(72) Inventors: Honghua Yang, Santa Barbara, CA (US); Craig Prater, Santa Barbara, CA (US)

(73) Assignee: Bruker Nano, Inc., Santa Barbara, CA (US)

( * ) Notice: Subject to any disclaimer, the term of this patent is extended or adjusted under 35 U.S.C. 154(b) by 0 days.

(21) Appl. No.: 15/917,210

(22) Filed: Mar. 9, 2018

(65) Prior Publication Data

US 2018/0259553 A1    Sep. 13, 2018

Related U.S. Application Data

(60) Provisional application No. 62/469,349, filed on Mar. 9, 2017.

(51) Int. Cl.
*G01Q 60/18*    (2010.01)
*G01N 21/65*    (2006.01)
*G01N 21/39*    (2006.01)
*G01Q 30/02*    (2010.01)
*G01Q 60/22*    (2010.01)

(52) U.S. Cl.
CPC ............. *G01Q 60/18* (2013.01); *G01N 21/39* (2013.01); *G01N 21/658* (2013.01); *G01Q 30/02* (2013.01); *G01Q 60/22* (2013.01)

(58) Field of Classification Search
CPC ........ G01G 60/18; G01G 30/02; G01G 60/22; G01N 21/39; G01N 21/658
USPC ....................................................... 850/30, 21
See application file for complete search history.

(56) References Cited

U.S. PATENT DOCUMENTS

| 8,402,819 | B2 * | 3/2013 | Dazzi | B82Y 35/00 73/105 |
| 2014/0289912 | A1 * | 9/2014 | Andreev | B82Y 35/00 850/18 |

* cited by examiner

*Primary Examiner* — Nicole M Ippolito
*Assistant Examiner* — Hanway Chang
(74) *Attorney, Agent, or Firm* — Boyle Fredrickson S.C.

(57) ABSTRACT

Systems and methods may be provided for measuring an infrared absorption of a sub micrometer region of a sample. An Infrared light source may illuminate a sample in a region that is interacting with the tip of a Scanning Probe Microscope (SPM), stimulating the sample in a way that produces measurable optical properties related to Infrared absorption of the sample region. A probe light source is directed at the region of the sample and SPM tip, and probe light emanating from the tip and sample region is collected. The collected light may be used to derive infrared absorption spectrum information of the sample region, possibly on a sub-micron scale.

20 Claims, 7 Drawing Sheets

FIG. 1A

FIG. 1B
Inset

METHOD AND APPARATUS FOR INFRARED SCANNING NEAR-FIELD OPTICAL MICROSCOPY BASED ON PHOTOTHERMAL EFFECT

RELATED APPLICATION

The present application claims the benefit of U.S. Provisional Application No. 62/469,349 filed Mar. 9, 2017, which is hereby incorporated herein in its entirety by reference.

BACKGROUND

The specification relates to Scanning Near Field Optical Microscopy (SNOM) and in particular to Infrared (IR) SNOM for acquiring information indicative of the optical properties and/or material composition of a surface that directly correlates to infrared absorption spectrum.

s-SNOM and in particular s-SNOM performed in the IR may be a useful technique for measuring and mapping optical properties/material composition of some surfaces with resolution approaching nanometer scale. Various aspects of the technique are described in U.S. applications Ser. Nos. 13/835,312, 14/322,768, 14/634,859, 14/957,480, and 15/249,433 by common inventors and commonly owned with this application. These applications are incorporated by reference in their entirety. AFM-IR may be a useful technique for measuring and mapping optical properties/material composition of some surfaces with resolution approaching nanometer scale. Various aspects of the technique are described in U.S. Pat. Nos. 8,869,602, 8,680,457, 8,402,819, 8,001,830, 9,134,341, 8,646,319, 8,242,448, and U.S. patent application Ser. Nos. 13/135,956 and 15/348,848 by common inventors and commonly owned with this application. These applications are incorporated by reference in their entirety.

SUMMARY

Systems and methods may be provided for measuring an infrared absorption of a sub-micrometer region of a sample. An infrared light source may illuminate a sample in a region that is interacting with the tip of a Scanning Probe Microscope (SPM), stimulating the sample in a way that produces measurable changes in the optical properties related to infrared absorption of the sample region. A probe light source is directed at the region of the sample and SPM tip, and probe light emanating from the sample region in the vicinity of the SPM tip is collected. The collected light may be used to derive infrared absorption spectrum information of the sample region, including on a sub-micron scale.

In one aspect a method may be provided for measuring an infrared absorption spectrum of a region of a sample, the method may include the steps of interacting a tip of a Scanning Probe Microscope (SPM) with the sample region; illuminating the sample region with an infrared beam from an infrared light source; illuminating the sample region and the SPM tip with probe light from a narrow band light source; collecting probe light emanating from the sample region; and analyzing the collected probe light to construct a signal indicative of the infrared absorption spectrum of the sample region.

In one embodiment of the first aspect, the narrow band light source may be characterized by an optical bandwidth and wherein optical properties of the sample may be substantially constant within the bandwidth of the narrow band light source. In another embodiment of the first aspect, the bandwidth of the narrow band light source may be less than 8 cm$^{-1}$. In one embodiment of the first aspect, a center wavelength of the narrowband light source may be less than 2 microns.

In another embodiment of the first aspect, the infrared light source comprises a tunable infrared laser. In one embodiment of the first aspect, the method may further include the step of repeating the above steps at a plurality of center wavelengths of the infrared light source. In another embodiment of the first aspect, the infrared light source may be a broadband source including a globar or a femto-second laser. In one embodiment of the first aspect, the method may further include the step of using a Fast Fourier Transform to construct a spectrum from the broadband source.

In another embodiment of the first aspect, dispersive contributions from a real index of refraction of the sample region may be suppressed. In one embodiment of the first aspect, the infrared absorption spectrum may be measured with a spatial resolution of less than 1 micron. In another embodiment of the first aspect, the infrared absorption spectrum may be measured with a spatial resolution of less than 100 nm. In one embodiment of the first aspect, the infrared absorption spectrum may be measured with a spatial resolution of less than 10 nm.

In another embodiment of the first aspect, the infrared beam may illuminate the sample from an oblique angle from above the sample. In one embodiment of the first aspect, the infrared radiation may illuminate the sample via total internal reflection. In another embodiment of the first aspect, the infrared beam may be modulated at a frequency $f_{IR}$, and wherein the analyzing step may include demodulating an amplitude of the collected probe light at a frequency $n \times f_{IR}$ where n is an integer. In one embodiment of the first aspect, the modulation frequency $f_{IR}$ may exceed 1 kHz.

In another embodiment of the first aspect, the infrared absorption spectrum may be calculated using an amplitude of the collected probe light with the SPM probe in contact and out of contact with the sample surface. In one embodiment of the first aspect, the interacting step may include oscillating the SPM probe at a resonance frequency $f_O$ of the SPM probe. In another embodiment of the first aspect, the collected probe light is demodulated at a frequency $n \times f_O$ where n is an integer.

In one embodiment of the first aspect, at least a portion of the collected probe light may be sent to a Raman spectrometer. In another embodiment of the first aspect, probe light collected by the Raman spectrometer may be used to perform tip enhanced Raman spectroscopy at the same sample region as the infrared absorption spectrum.

In one embodiment of the first aspect, the narrow band light source may have a center wavelength substantially equal to one of the following: 244 nm, 257 nm, 325 nm, 364 nm, 457 nm, 473 nm, 488 nm, 514 nm, 532 nm, 633 nm, 660 nm, 785 nm, 830 nm, 980 nm, and 1064 nm. In another embodiment of the first aspect, an intensity of the collected probe light may vary due to changes in reflectivity of the sample region due to the absorption of infrared light by the sample region.

In one embodiment of the first aspect, at least a portion of the collected probe light may be filtered by at least one fluorescence filter and the filtered light analyzed to determine a fluorescent response of the sample. In another embodiment of the first aspect, the demodulation step may be performed at multiple integer values of n. In one embodiment of the first aspect, the demodulation at multiple integer values of n is used to construct a depth resolved tomographic measurement of the sample.

In a second aspect, a system may be provided for measuring an infrared absorption of a region of a sample, including an SPM with a probe tip, infrared light source, a narrow band probe light source, a probe light collector, and at least one computing device including control, data acquisition and data analysis elements, the system configured to: interact the tip of the SPM with the sample region; illuminate the sample region with an infrared beam from the infrared light source; illuminate the sample region and the SPM tip with the narrow band probe light beam; collect probe light from the sample region with probe light detector; and analyze the collected probe light to construct a signal indicative of the infrared absorption spectrum of the sample region.

In one embodiment of the second aspect, the system may further include a modulator and a demodulator, further configured to: modulate an intensity of the infrared radiation; and demodulate the collected probe light to determine an amplitude of collected probe light, wherein the amplitude of the collected probe light is used to construct the infrared absorption spectrum of the submicron region of the sample. In another embodiment of the second aspect, the infrared light source may include a tunable infrared laser. In one embodiment of the second aspect, the source of infrared radiation may include a quantum cascade laser. In another embodiment of the second aspect, the source of probe light may include at least one of: a visible laser, a near-infrared laser, a mid-infrared laser, and an ultraviolet laser. In one embodiment of the second aspect, the infrared light source may include a broadband source including a globar or a femto-second laser.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

Inset

DETAILED DESCRIPTION OF ILLUSTRATIVE EMBODIMENTS

In some embodiments, systems and methods may be provided to suppress the background scattering contribution to scattering-type Scanning Near field Optical Microscopy (s-SNOM) measurements. The SPM probe-sample area is illuminated by a light source. In some embodiments the light source is tunable allowing for the illumination to occur at a plurality of selected wavelengths, one wavelength at a time. The measurements may be repeated at a plurality of illumination wavelengths and/or at a plurality of sample positions.

Definitions

"Optical property" refers to an optical property of a sample, including but not limited to index of refraction, absorption coefficient, reflectivity, absorptivity, real and/or imaginary components of the index refraction, real and/or imaginary components of the sample dielectric function and/or any property that is mathematically derivable from one or more of these optical properties.

A "scanning probe microscope (SPM)" refers to a microscope where a sharp probe is interacted with a sample surface and then scanned over the surface while measuring one or more properties of the sample surface. The scanning probe microscope may be an Atomic Force Microscope (AFM), which may include cantilever probe with a sharp tip. The SPM generally include a capability for measuring the motion, position, and or other response of the probe tip and/or an object to which the probe tip is attached, e.g. a cantilever or a tuning fork or MEMS device, for example. The most common method includes using an optical lever system where a laser beam is bounced off the cantilever probe to measure deflection of the cantilever. Alternatives include self-sensing techniques like piezoresistive cantilevers, tuning forks, capacitive sensing, and other techniques. Other detection systems may measure other properties such as force, force gradient, resonant frequency, temperature, and/or other interactions with the surface or responses to the surface interaction. The SPM may also use aperture based probes that can be used to deliver light to and/or collect light from the sample.

"Interacting a tip of an SPM probe with the sample region" refers to bringing the SPM probe tip close enough to the surface of a sample such that one or more near field interactions occur, for example the attractive and/or repulsive tip-sample forces, and/or the generation and/or amplification of radiation scattered from an area of the sample in proximity of the probe apex. The interaction can be contact mode, intermittent contact/tapping mode, non-contact mode, shear force mode, pulsed force mode, and/or any lateral modulation mode. The interaction can be constant or in some cases, periodic. The periodic interaction may be sinusoidal or any arbitrary periodic waveform. Pulsed force modes and/or fast force curve techniques may also be used to periodically bring the probe to a desired level of interaction with a sample, followed by a hold period, and then a subsequent probe retraction.

"Illuminating" means to direct radiation at an object, for example a surface of a sample, the probe tip, and/or the region of probe-sample interaction. Illumination may include radiation in the infrared wavelength range, visible, and other wavelengths from ultraviolet to THz. Illumination may include any arbitrary configuration of radiation sources, reflecting elements, focusing elements and any other beam steering or conditioning elements.

"Infrared light source" refers to one or more optical sources that generate or emits radiation in the infrared wavelength range, generally in the mid-IR between 2-25 microns. An infrared light source may generate radiation over this full range, or in many cases, have a tuning range that is a subset of this range, for example 2.5-4 microns, or 5-13 microns, for example. The radiation source may be one of a large number of sources, including thermal or Globar sources, supercontinuum laser sources, frequency combs, difference frequency generators, sum frequency generators, harmonic generators, optical parametric oscillators (OPOs), optical parametric generators (OPGs), quantum cascade lasers (QCLs), nanosecond, picosecond, femtosecond, and attosecond laser systems, CO2 lasers, heated cantilever probes or other microscopic heaters, and/or any other source that produces a beam of radiation. The source emits infrared radiation in some cases, but it can instead or also emit in other wavelength ranges, for example from ultraviolet to THz. The source may be narrowband, for example with a spectral width of <10 cm$^{-1}$ or <1 cm$^{-1}$ less, or may be broadband, for example with a spectral width of >10 cm$^{-1}$, >100 cm$^{-1}$ or greater than 500 cm$^{-1}$.

"Probe light source" refers to a radiation source that is used to probe the response of the sample to the incidence of light from the infrared light source. The radiation source may comprise a gas laser, a laser diode, a superluminescent diode (SLD), a near infrared laser, a UV and/or visible laser beam generated via sum frequency or difference frequency generation, for example. It may also comprise any or other sources of near-infrared, UV and/or visible light that can be focused to a spot on the scale smaller than 2.5 micrometer, and or even smaller than 1 micrometer, and possibly smaller than 0.5 micrometer. In some embodiments, the probe light source may operate at a wavelength that is outside the tuning or emission range of the infrared light source, but the probe light source can also be a fixed wavelength source at a select wavelength that does in fact overlap with the tuning range of the infrared light source. A "probe light beam" is a beam originally enlitted from a probe light source. In some embodiments, the probe light source is selected to be a "narrow band light source," as described below.

"Collecting probe light" refers to collecting radiation of a probe light beam that has interacted with a sample. The probe light can be collected after reflection, scattering, transmission, evanescent wave coupling, and/or transmission through an aperture probe.

"Signal indicative of refers to a signal that is mathematically related to a property of interest. The signal may be an analog signal, a digital signal, and/or one or more numbers stored in a computer or other digital electronics." The signal may be a voltage, a current, or any other signal that may be readily transduced and recorded. The signal may be mathematically identical to the property being measured, for example explicitly an absolute phase signal or an absorption coefficient. It may also be a signal that is mathematically related to one or more properties of interest, for example including linear or other scaling, offsets, inversion, or even complex mathematical manipulations.

"Spectrum" refers to a measurement of one or more properties of a sample as a function of wavelength or equivalently (and more commonly) as a function of wavenumber.

"Infrared absorption spectrum" refers to a spectrum that is proportional to the wavelength dependence of the infrared absorption coefficient, absorbance, or similar indication of IR absorption properties of a sample. An example of an infrared absorption spectrum is the absorption measurement produced by a Fourier Transform Infrared spectrometer (FTIR), i.e. an FTIR absorption spectrum. (Note that IR absorption spectra can also easily be derived from transmission spectra.)

"Dispersive contributions" refers to any contribution of signal due to the real part of the refractive index, or more generally effects that are not resulting from solely the absorptive properties of the sample.

"Real index of refraction" refers to the real part of the refractive index of a material.

"Modulating" or "modulation" when referring to radiation incident on a sample refers to periodically changing the infrared laser intensity at a location periodically. Modulating the light beam intensity can be achieved by means of mechanical chopping of the beam, controlled laser pulsing, and/or deflecting the laser beam, for example by a tilting mirror that is driven electrostatically, electromagnetically, with piezo actuators or other means to tilt or deform the mirror. Modulation can also be accomplished with diffraction effects, for example by diffractive MEMS-based modulators or by high speed shutters, attenuators, or other mechanisms that change the intensity, angle, and/or phase of the laser intensity incident on the sample.

"Demodulate" or "demodulation" refers to extracting an information-bearing signal from an overall signal, usually, but not necessarily at a specific frequency. For example in this application, the collected probe light collected at a photo detector represents an overall signal. The demodulation process picks out the portion that is being perturbed by infrared light absorbed by the sample. Demodulation can be accomplished by a lock-in amplifier, a fast Fourier transform (FFT), a calculation of a discrete Fourier component at a desired frequency, a resonant amplifier, a narrow band bandpass filter, or any other technique that largely enhances the signal of interest while suppressing background and noise signals that are not in sync with the modulation. A "demodulator" refers to a device or system that performs demodulation.

"Aperture based probe" or 'aperture probe' refers to a scanning probe microscope probe fabricated with an aperture to transmit and or collect light through the aperture. The aperture based probe can be a cantilever probe, or other type of probe body, and/or tapered fiber probe. Probes have also been fabricated from metals and polymeric materials and etched MEMS structures. An SPM probe tip with a hole through the probe body and tip may also serve as an aperture probe. In general the probe only needs to have a means to guide light through a sub-wavelength aperture and a sharp tip that can interact with the sample and support for some mechanism to detect the interaction, e.g. by the bending of a cantilever probe, or the change in resistance, resonance frequency or other property that is indicative of the interaction between the probe time and the sample.

An "SPM controller" refers to a system to facilitate data acquisition and control of the AFM-IR system. The controller may be a single integrated electronic enclosure or may comprise multiple distributed elements. The control elements may provide control for positioning and/or scanning of the probe tip and/or sample. They may also collect data about the probe deflection, motion or other response, provide control over the radiation source power, polarization, steering, focus and/or other functions. The control elements etc. may include a computer program method or a digital logic method and may be implemented using any combination of a variety of computing devices (computers, Personal Electronic Devices), analog and/or digital discrete circuit components (transistors, resistors, capacitors, inductors, diodes, etc.), programmable logic, microprocessors, microcontrollers, application-specific integrated circuits, or other circuit elements. A memory configured to store computer programs and may be implemented along with discrete circuit components to carry out one or more of the processes described herein.

A "lock-in amplifier" is one example of a "demodulator" (defined above) and is a device, system, and/or an algorithm that demodulates the response of a system at one of more reference frequencies. Lock-in amplifiers may be electronic assemblies that comprise analog electronics, digital electronics, and combinations of the two. They may also be computational algorithms implemented on digital electronic devices like microprocessors, field programmable gate arrays (FPGAs), digital signal processors, and personal computers. A lock-in amplifier can produce signals indicative of various metrics of an oscillatory system, including amplitude, phase, in phase (X) and quadrature (Y) components or any combination of the above. The lock-in amplifier in this context can also produce such measurements at both the reference frequencies, higher harmonics of the reference frequencies, and/or sideband frequencies of the reference frequencies.

A "detector" in the context of the probe light beam, refers to an optical detector that produces a signal indicative of the amount light incident on the detector. The detector can be any of a large variety of optical detectors, including but not limited to a silicon PIN photodiode, a gallium phosphide photodetector, other semiconducting detectors, an avalanche photodiode, a photomultiplier tube, and/or other detector technologies that produce a signal indicative of the amount of light incident on the detector surface. The detector can also be fluorometers and/or Raman spectrometers. "Narrowband Light source" a light source with a narrow bandwidth or linewidth, for example a light of linewidth smaller than 8 cm$^{-1}$, but in general it can be a light source with a linewidth narrow enough that the linewidth does not cover a spectral range of interest of the sample.

The current disclosure is directed towards obtaining measurements of infrared optical properties of a material on a length scale much, much smaller than the diffraction limit of the infrared wavelengths employed, and in fact down to the nanometer scale. The current approach can also directly measure the infrared absorption spectrum of a sample with nanometer scale resolution, while avoiding dispersive artifacts that have inhibited other SNOM based techniques. This is achieved by arranging a near-field detection system where the collected scattered probe light signal at a different wavelength than the IR light is proportional to a temperature rise in the sample that is in turn dependent on the amount of IR light absorbed by the sample in the vicinity of an SPM probe tip.

Figures 1A, 1B:
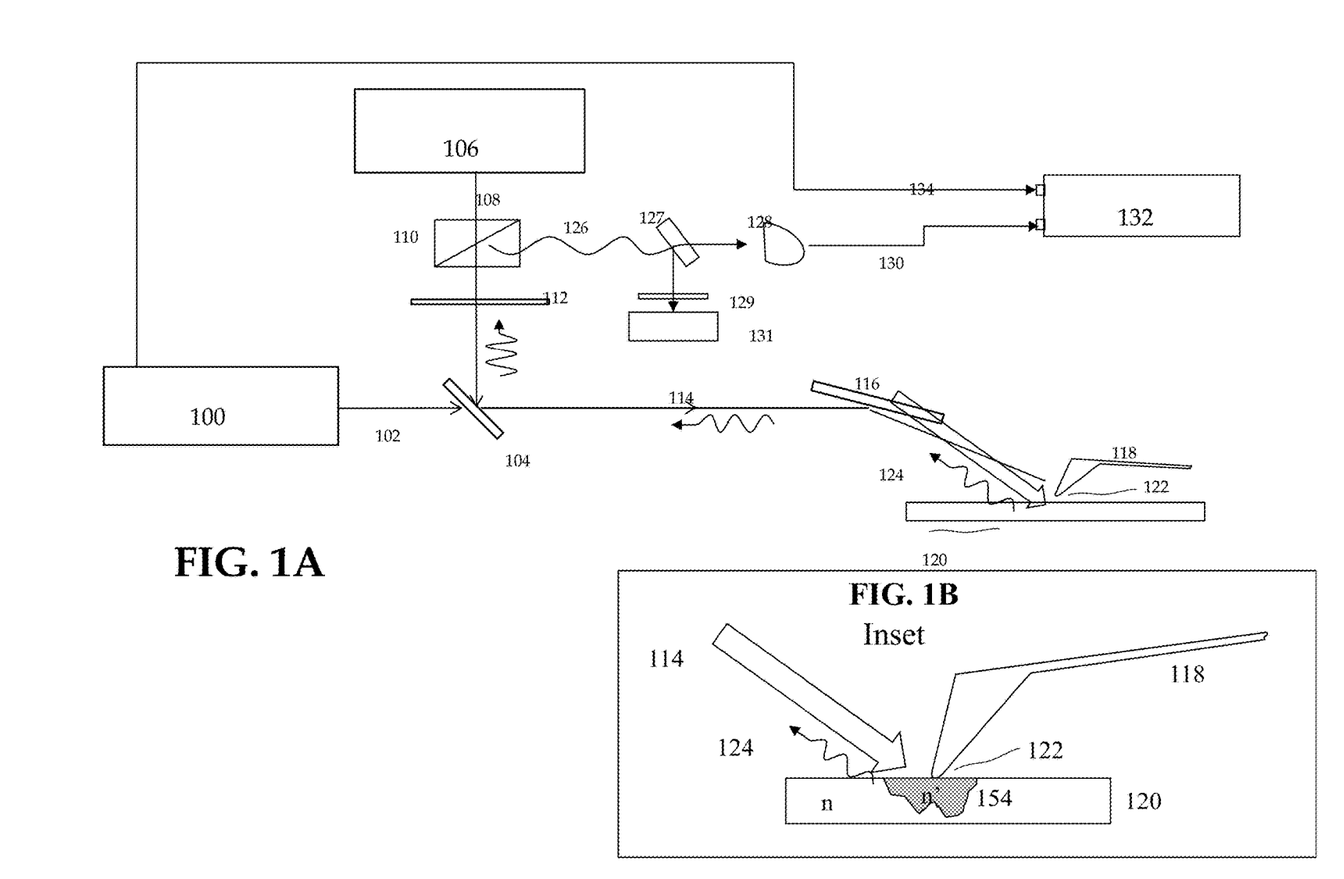
FIG. 1A shows a simplified schematic of an exemplary embodiment.
FIG. 1B illustrates the measurement of a scattered probe light, according to an illustrative embodiment.

FIG. 1A shows a simplified schematic of an illustrative embodiment. Infrared beam 102 is emitted from an infrared light source 100 towards a beam combiner 104. The infrared beam is modulated at a frequency $f_{IR}$. A probe light beam 108 emitted from a probe light source 106, for example a visible laser, is reflected off the beam combiner 104. The beam combiner 104 may be a dichroic mirror that transmits infrared beam 102 while reflects visible, but it may also reflect infrared beam and transmit visible, or combine whatever wavelengths are utilized. Combined beam 114 after the beam combiner 104 continues towards a focusing optic 116 that focuses the beam onto a sample 120 in the vicinity of the tip 122 of a probe 118 of a scanning probe microscope (SPM). The scattered probe light 124, i.e. the light emanating from the region, may be collected by the same focusing optics 116 (or by some other optics), and then directed to a quarter waveplate 112, such that the polarization is rotated 90 degrees relative to the incident beam. Then a polarizing beamsplitter 110 separates out the polarization rotated beam 126 from the incidence beam and directs it towards a detector 128. The signal output from the detector 130 is analyzed by a demodulator 132, which may be a lock-in amplifier. The demodulator 132 demodulates at the frequency of the IR light modulation frequency $f_{IR}$ 134, or at a harmonic of $f_{IR}$ (i.e., m×$f_{IR}$, with m an integer). In one embodiment, a filter 127 can split out part of the beam 126 and direct to a fluorescence or Raman spectrometer 131 for collecting fluorescent or Raman signal of the sample. A fluorescent or Raman filter 129 can be used to filter out the beam at the probe light wavelength.

Inset diagram FIG. 1B shows an enlarged view of the probe and sample region. An incoming infrared beam 114 (a component of combined beam 114 in FIG. 1) is incident on the sample 120 in the vicinity of the SPM probe tip 122. Any absorption of IR light from IR beam 114 by the sample causes a local temperature rise ΔT that is roughly proportional to the amount of light absorbed. The change in temperature in the heated region 154 causes a change in the refractive index from n to n'=n+Δn (as well as thermal expansion of the sample). The amplitude of the scattered probe light beam 124 is dependent on the reflectivity of the sample region 154 (as well as the properties of the SPM probe 118). As the temperature and refractive index of the sample region 154 changes, so does the reflectivity of the sample region. Consequently, the amplitude of the scattered probe light 124 is perturbed by this change in the refractive index Δn due to the IR absorption by the sample region 154. This change in the amplitude of scattered probe light can thus be used to construct a signal that is proportional to the sample infrared absorption property.

Referring back to FIG. 1A, in one embodiment the IR laser 100 is at least modulated at one frequency $f_{IR}$ to create a periodic fluctuation in the temperature of the sample 120 due to the absorption of IR radiation by the sample. As discussed above, this can result in a fluctuation in the amount of probe light scattered from the sample 124 and also a fluctuation in the intensity of light 126 detected by detector 128. In one embodiment the signal produced by detector 128 is sent to a demodulator 130 that demodulates an amplitude of light collected by detector 130 at a frequency related to the modulation frequency $f_{IR}$ of the IR laser beam. The demodulation can be performed at $f_{IR}$ directly, and at a harmonic of $f_{IR}$ (i.e. m×$f_{IR}$ where m is an integer). Demodulation can also be performed at sideband frequencies that combine the IR laser modulation frequency with the frequency of a secondary modulation, for example the oscillation of the SPM tip at a frequency $f_O$.

Referring back to FIG. 1A, infrared light source 100 may be any of a large variety of IR light sources as described in the definition of "infrared light source". In one embodiment it is a pulsed infrared laser, for example a narrow-band tunable laser. In one embodiment the IR light source is a pulsed quantum cascade laser (QCL). Alternately it may be a CW infrared laser with an integrated or external modulator. Beam combiner 102 can be an optical component that passes the IR light and reflects the probe beam or the reverse where it reflects IR light and transmits visible (in which case the orientation of the IR and probe light beams and beam combiner would be appropriately adjusted.) Focusing optic 116 can be a single optical element, for example a lens or a parabolic mirror or may be a system of optical components including an arbitrary number of lenses and/or mirrors, diffractive components, etc. to deliver focused IR and visible light beams to the sample 120 in the vicinity of the SPM probe tip 122.

The use of a polarizing beam splitter 110 and quarter waveplate 112 makes for an efficient way to separate the incoming and outgoing probe beams base on polarization, but other schemes may also be employed. For example a simple beamsplitter can be used without a quarter waveplate. Alternately, a separate optical path can be used to collect forward scattered light or light from a different solid angle that focusing optics 116.

Detector 128 can be any of a large variety of optical detectors as described in the definitions section, depending on the wavelength and intensity of probe light and the bandwidth desired for a specific measurement.

The apparatus can also include additional filters, detectors, and spectrometers to enable simultaneous or sequential Raman spectroscopy and/or fluorescence measurements. In these cases, one or more optional fluorescence and/or Raman filters 129 can be installed to substantially block light at the probe light source center wavelength and pass light that is wavelength shifted from the probe wavelength. This approach allows detection of inelastically scattered light, including but not limited to Raman and fluorescently shifted light. Additional optional detectors can be used to detect and/or spectrally analyze the wavelength shifted light. Specifically, a Raman spectrometer can be used to measure Raman spectra from light that emanates from the tip-sample region due to the excitation by the probe light beam.

Figure 6:
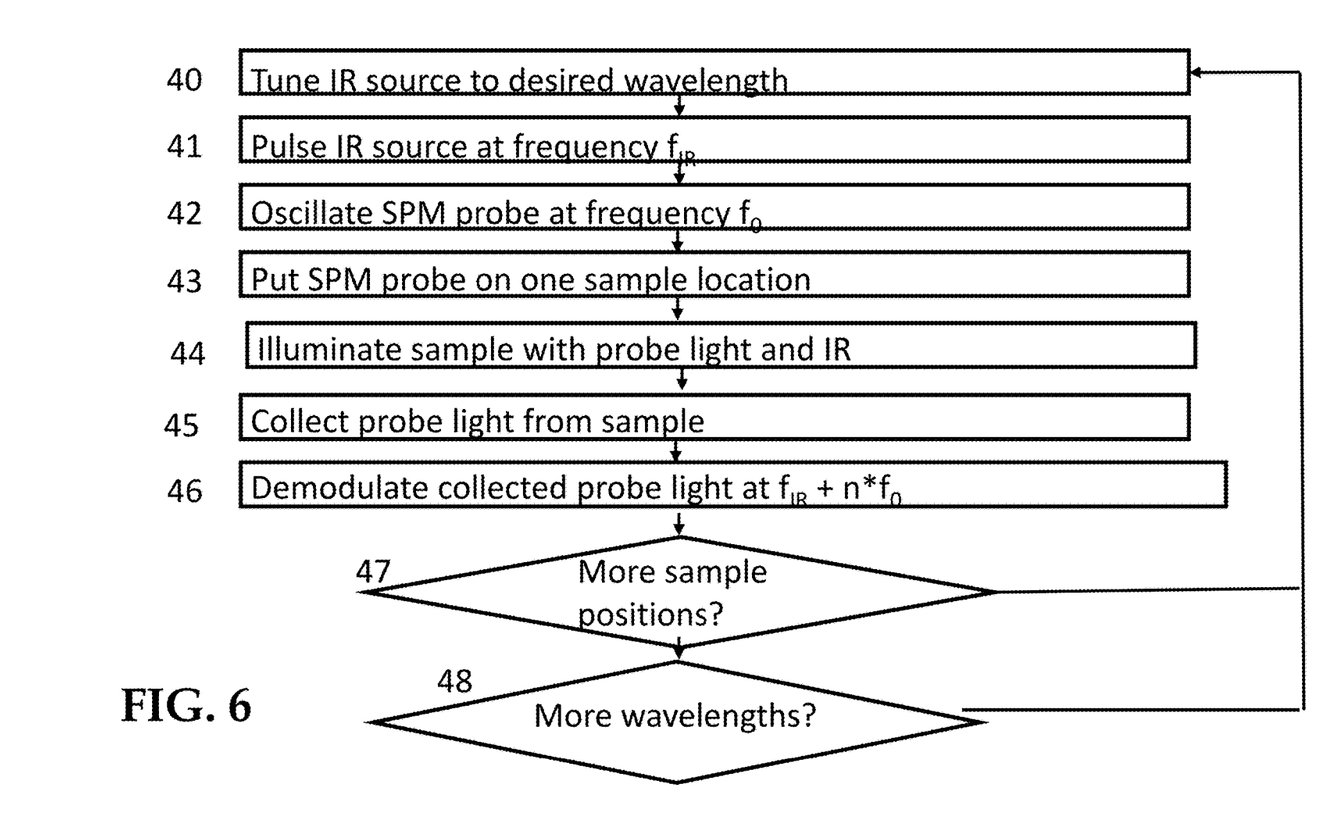
FIG. 6 is a flow chart of a method, according to an illustrative embodiment.

A flow chart of an illustrative method is shown in FIG. 6. In step 60, an IR light source is tuned to a desired wavelength. In step 61, the IR light source is pulsed at a frequency $f_{IR}$. Note that this may be achieved by an internal pulse controller or an external chopper. In step 62 the SPM probe oscillates at a frequency $f_O$, in some embodiment, $f_O$ can be 0 Hz. In step 63, the SPM probe tip is put down on the sample. Note that this may be achieved by moving the tip or the sample or a combination of both. Then in step 64, the IR light and a probe light is used to illuminate a region of the sample in the vicinity of the SPM probe tip. In step 65, scattered probe light from the sample is collected and 66 the collected probe light is then being demodulated to construct a signal at a frequency $m \times f_{IR} + n \times f_O$, with m and n integers. This measurement can be repeated at any number of different positions on the sample (step 67) and/or wavelengths (step 68).

Figure 7:
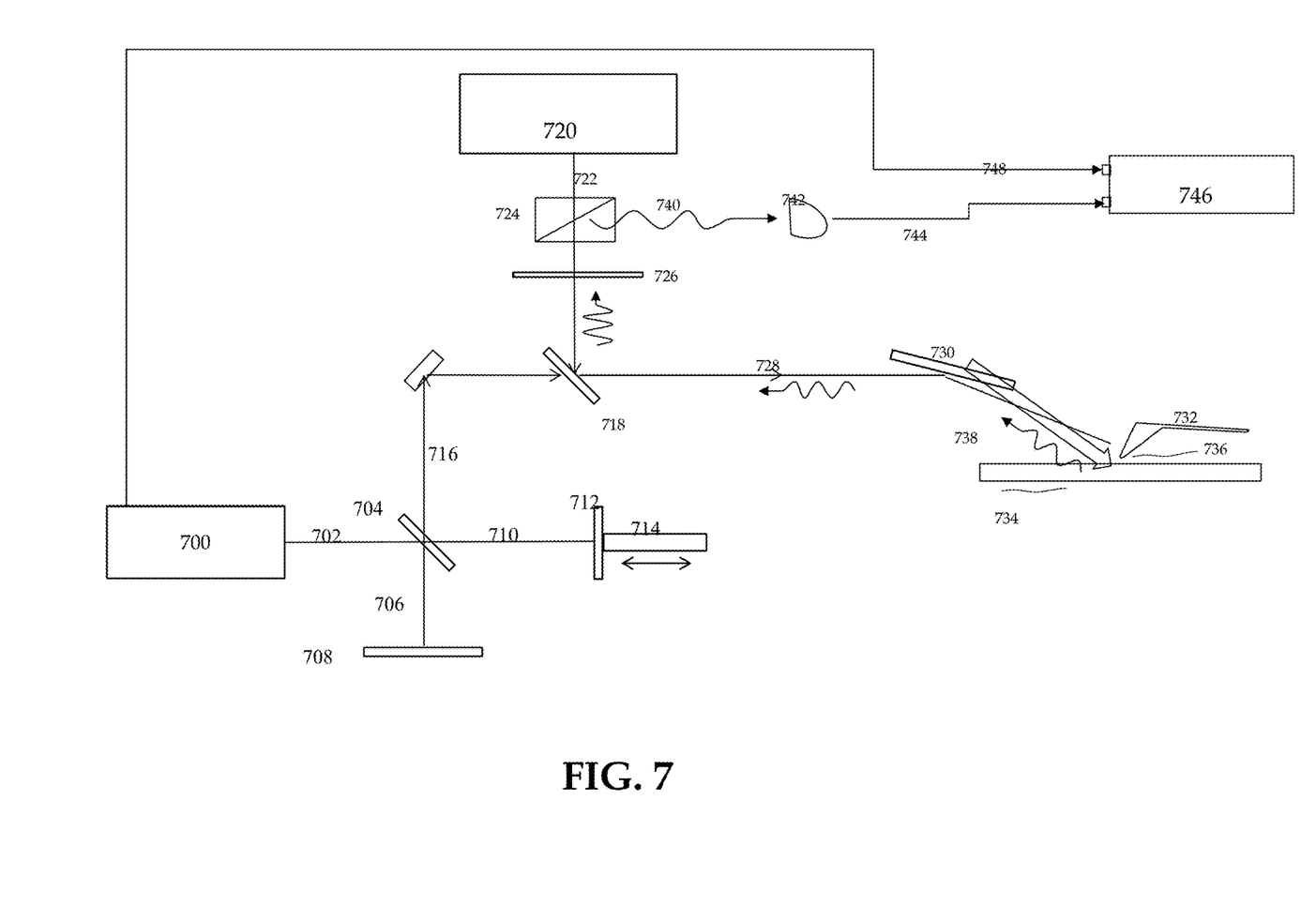
FIG. 7 shows an embodiment incorporating a broadband IR source.

FIG. 7 shows a modified implementation of FIG. 1A with the IR light source being a broadband light source. Infrared beam 702 is emitted from a broadband infrared light source 700 towards an IR beamsplitter 704. Part of the beam 706 is reflected towards a static mirror 708. Part of the beam transmits 710 towards a moving mirror 712 attached to a translation stage 714. Recombined beam 716 after the IR beamsplitter 704 is directed towards a beam combiner 718. The IR beamsplitter 704, the static mirror 708, and the moving mirror 712 forms as an interferometer for broadband spectrum detection. A probe light beam 722 emitted from a probe light source 720, for example a visible laser, is reflected off the beam combiner 718. The beam combiner 718 may be a dichroic mirror that transmits infrared beam 716 while reflects visible, but it may also reflect infrared beam and transmit visible, or combine whatever wavelengths are utilized. Combined beam 728 after the beam combiner 718 continues towards a focusing optic 730 that focuses the beam onto a sample 734 in the vicinity of the tip 736 of a probe 732 of a SPM. The scattered probe light 738, i.e. the light emanating from the region, may be collected by the same focusing optics 730 (or by some other optics) and then directed to a quarter waveplate 726, such that the polarization is rotated 90 degrees relative to the incident beam. Then a polarizing beamsplitter 724 separates out the polarization rotated beam 740 from the incidence beam and directs it towards a detector 742. The signal output from the detector 744 is analyzed by a demodulator 746, which may be a lock-in amplifier. The demodulator 746 demodulates at the frequency of the IR light modulation frequency $f_{IR}$ 748, or at a harmonic of $f_{IR}$ (i.e., $m \times f_{IR}$, with m an integer).

Different configurations or orientations of incoming and scattering light can be implemented. For example, the incoming light can be focused from the top side of the sample and the scattered light collected from the opposite side of the sample. Or the incoming light is incident from the bottom, while the scattered light collected from the top side. Any combination of orientations of incidence and scattered light can be adopted, with some configurations listed in FIGS. 2-5.

Figure 2:
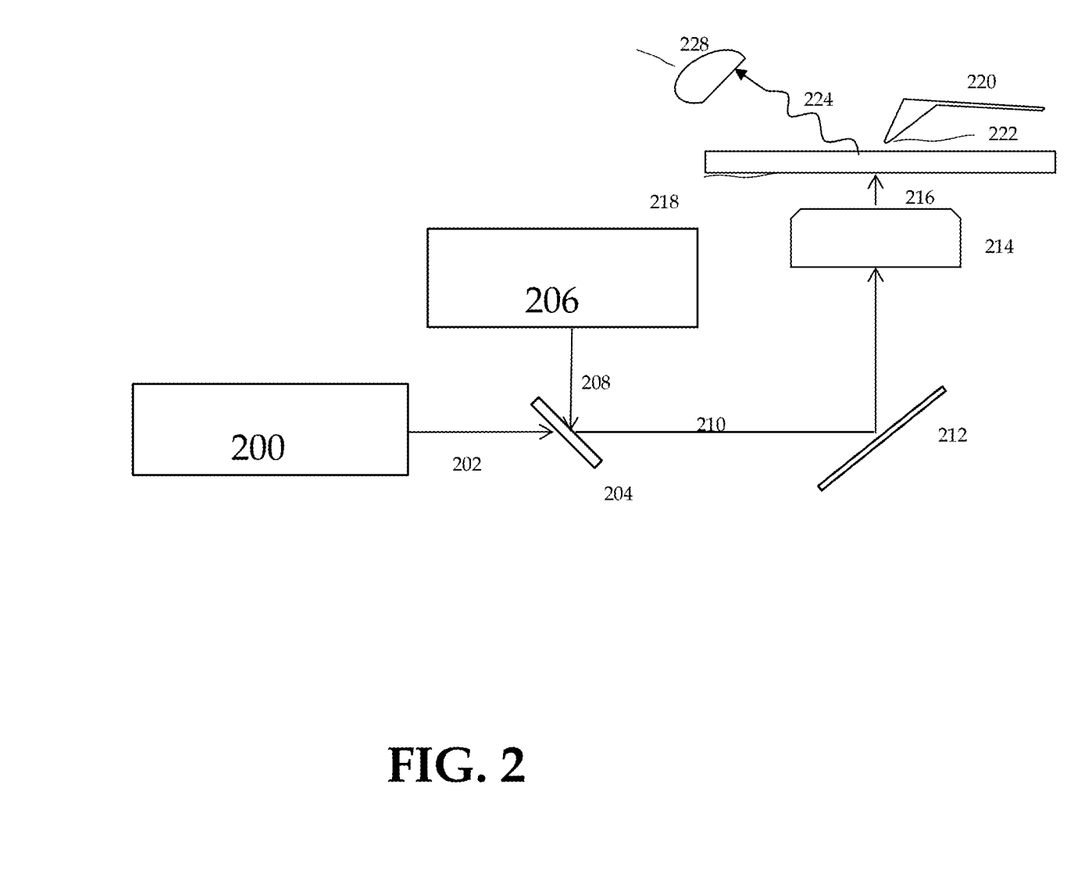
FIG. 2 an alternative implementation with bottom-up transmission geometry.

FIG. 2 shows an alternative implementation with bottom-up transmission geometry. Infrared beam 202 is emitted from an infrared light source 200 towards a beam combiner 204. A probe light beam 208 emitted from a probe light source 206, is reflected off the beam combiner 204. Combined beam 210 after the beam combiner 204 is guided by some optics 212 to an objective 214 for focusing. A dark field objective may be used to reduce the directly illuminated probe light beam to increase the modulation to improve the Signal to Noise (S/N). The focused beam 216 illuminates a sample 218 in the vicinity of the end 222 of a probe 220 of a probe microscope. The scattered, or emanated, probe light 224 is collected and detected by a detector 228. The principle of extracting infrared absorption property of the sample from analyzing the scattered probe beam is the same as in FIG. 1 B.

Figure 3:
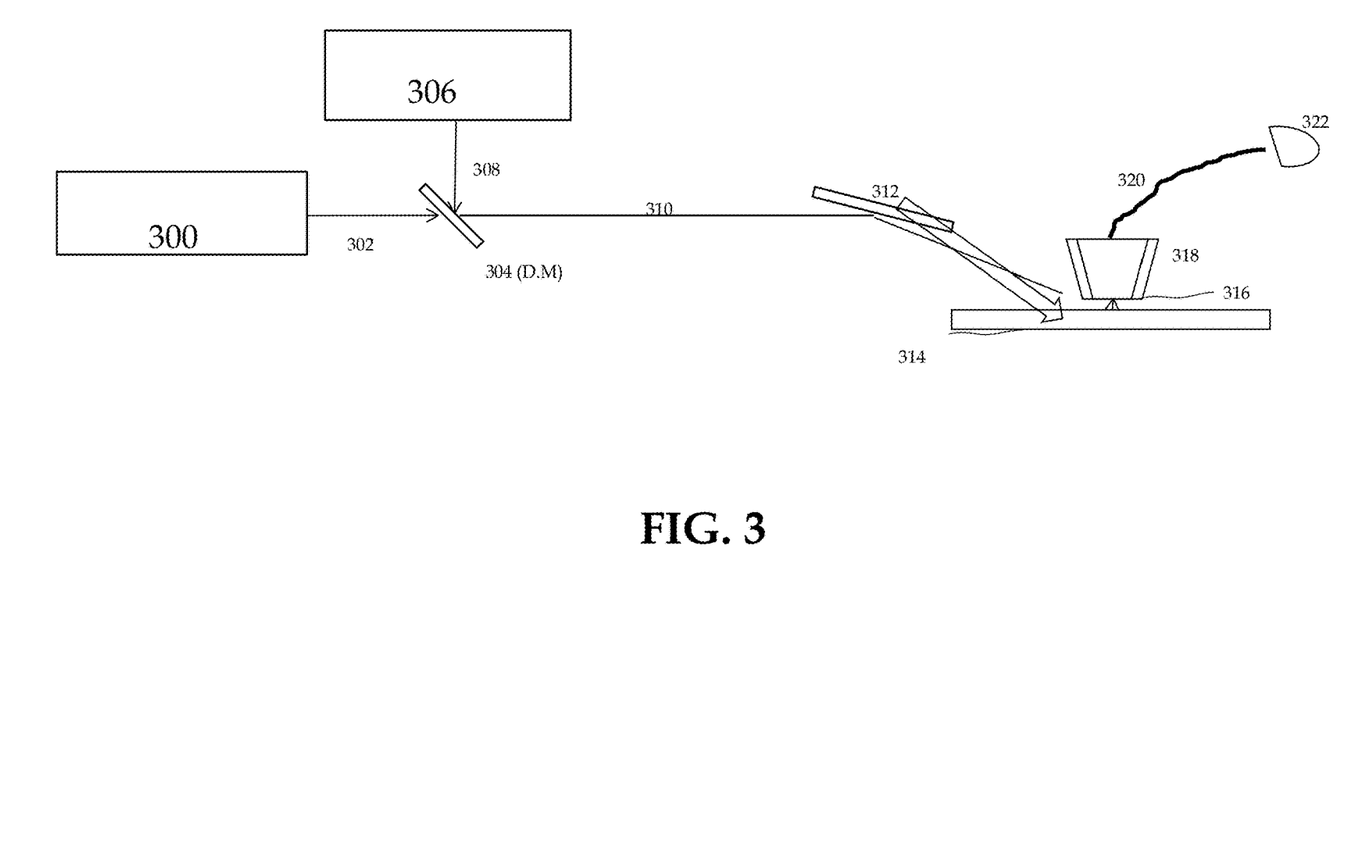
FIG. 3 shows an alternative implementation based on aperture-type scanning near-field optical microscopy.

FIG. 3 shows an alternative embodiment based on aperture-type scanning near-field optical microscopy. Infrared beam 302 is emitted from an infrared light source 300 towards a beam combiner 304. A probe light beam 308 emitted from a probe light source 306 is reflected off the beam combiner 304. Combined beam 310 after the beam combiner 304 continues towards a focusing optic 312 that focuses the beam onto a sample 314 in the vicinity of the tip of a probe 316 of an aperture probe microscope 318. The scattered probe light is collected through the aperture of the probe, and may be transmitted through a fiber or other optics 320 to a detector 322. The transmission of the signal from the aperture to the detector may also be done in free space.

Figure 4:
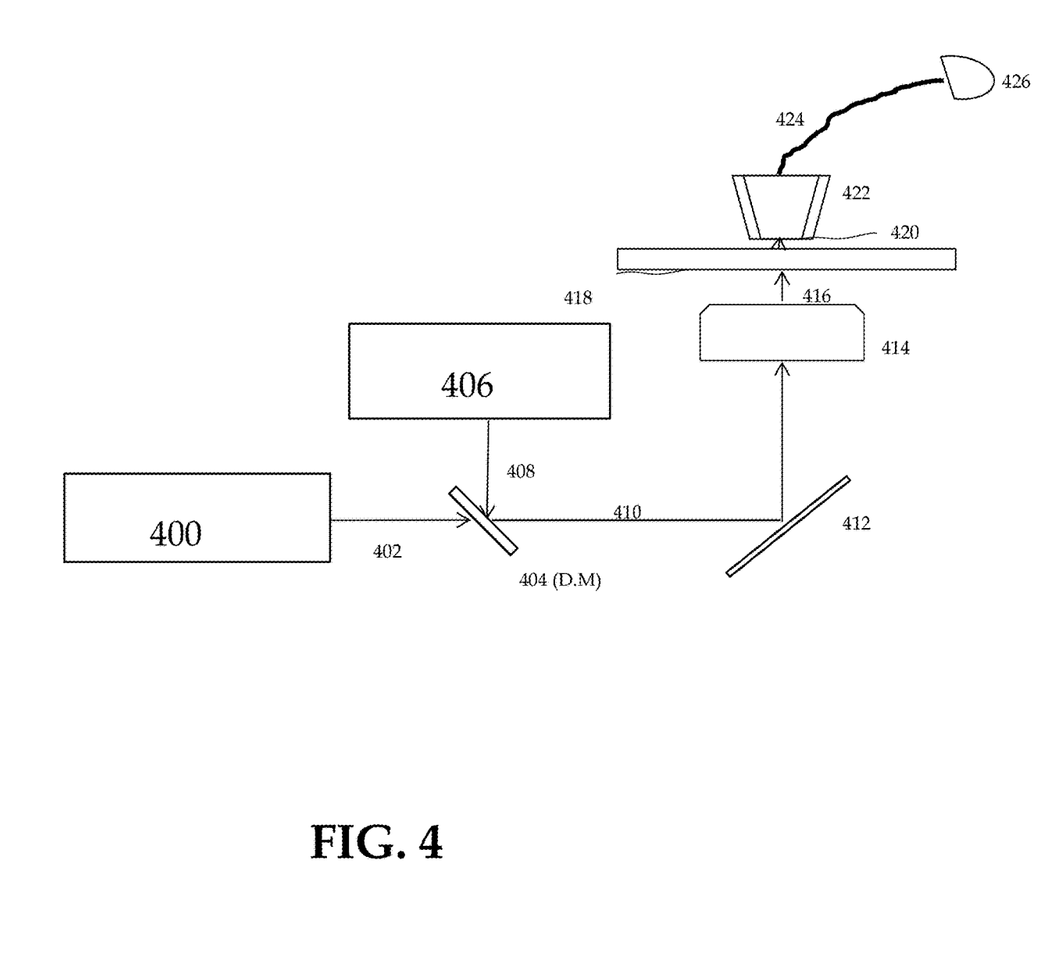
FIG. 4 shows another alternative implementation based on aperture-type scanning near-field optical microscopy.

FIG. 4 shows another alternative embodiment based on aperture-type scanning near-field optical microscopy. Infrared beam 402 is emitted from an infrared light source 400 towards a beam combiner 404. A probe light beam 408 emitted from a probe light source 406 is reflected off the beam combiner 404. Combined beam 410 after the beam combiner 404 is guided by some optics 412 to an objective 414 for focusing. The focused beam 416 illuminates a sample 418 in the vicinity of the tip of a probe 420 of an aperture probe microscope 422. The scattered probe light is collected through the aperture of the probe, and may be transmitted through a fiber and/or other optics 424 to a detector 426. The transmission of the signal from the aperture to the detector may also be done in free space.

Figure 5:
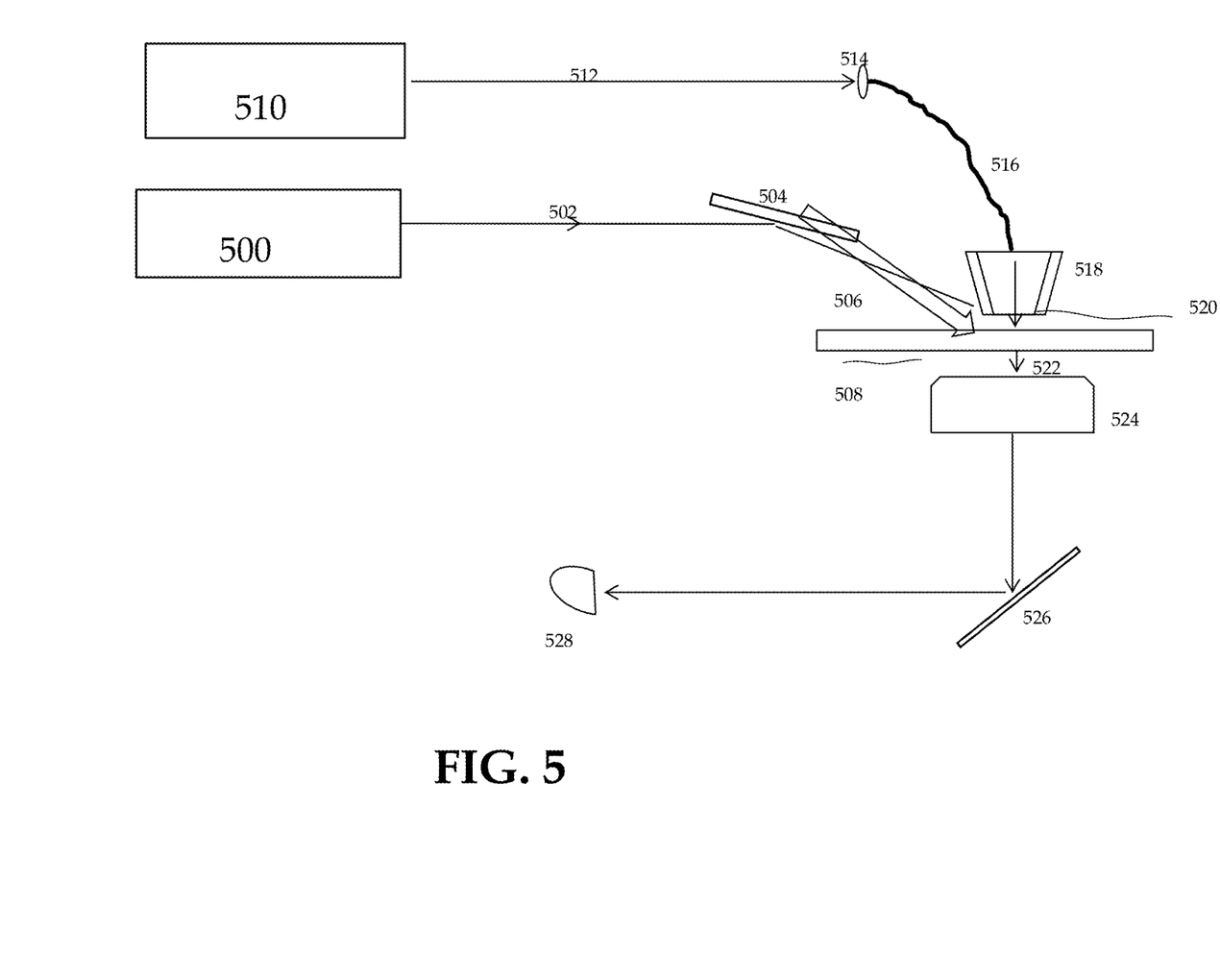
FIG. 5 shows another alternative implementation based on aperture-type scanning near-field optical microscopy.

FIG. 5 shows another alternative implementation based on aperture-type scanning near-field optical microscopy. Infrared light beam 502 is emitted from an infrared light source 500 towards a focusing optics 504. The focused infrared light beam 506 is focused onto a sample 508. A probe light beam 512 emitted from a probe light source 510 is guided by some optics 514 to an aperture based scanning near-field optical microscopy 516. The probe light beam 520 through the aperture 518 illuminates the same region as that of the focused infrared beam 506. The probe light 522 after passing through the sample is collected by an objective 524. The collected probe light is then guided by some optics 526 to a detector 528.

In this section we describe in more detail principles underlying the detection mechanism employed under certain embodiments. Note that this explanation is intended to be illustrative only and is not intended to limit the scope of the claims. More sophisticated analyses can be applied with the potential for higher accuracy, but the current discussion is just intended to describe one model that illustrates a mechanism for the detection scheme. One possible mechanism for the measurable IR absorption related optical property is change in index of refraction due to localized heating, which is a time dependent photothermal effect. A local temperature change due to illumination by an infrared light causes a refractive index change at the probe light wavelength). The local inhomogeneity of the refractive index causes a change in amplitude to the probe light scattering. The change in amplitude of the scattered probe light can be analyzed to construct an infrared absorption spectrum. The process is formulated as $$\Delta P \propto \frac{\sigma N}{k C_p} \frac{\partial n}{\partial T} P_{pr} P_{IR} \qquad \text{Eq. 1}$$

with absorption cross-section $\sigma$, number density N, heat conductivity k, heat capacity $C_p$, the refractive index at the probe wavelength n, the temperature T, the probe light power $P_{pr}$, the infrared light power $P_{IR}$. As an example to illustrate an achievable signal level, a temperature dependent change of the refractive index $$\frac{\partial n}{\partial T}$$

is on the order of $10^{-4}$/K for PMMA, polycarbonate, and water in the visible wavelength range (reference Cariou et al., Applied Optics Vol 25, No 3, 1986). This level of index change, however, is readily detectable using modulation and demodulation techniques. The spatial resolution achievable by some of the embodiments disclosed herein is much, much smaller than the diffraction limit of the infrared light source and is the same as in SNOM techniques discussed in the incorporated references. The resolution improvement come from a local enhancement of the incident radiation field due to the sharp SPM tip. The enhanced radiation field interacts with the sample and then scatters radiation into the far field. This near-field enhancement increases the amount of radiation scattered from the tip-sample region such that the scattered radiation can be more easily detected.

In comparison to conventional SNOM techniques based on directly detecting infrared light, the current disclosure is based on a probe light detection not from detection of the IR light. By detecting at the probe light, the non-local background scattering from the infrared light is suppressed, thus making some of the disclosed embodiments insensitive to the dispersive contributions of scattered light in the mid-IR.

The spatial resolution may be limited by thermal diffusion of the heated region after IR illumination to its surroundings. A fast modulation speed $f_{IR}$ may help to minimize thermal diffusion.

In one embodiment, the probe light wavelength may be chosen in a transparent region of the sample, so sample absorption is negligible. Thus probe light beam intensity can be increased to reduce photon noise. The infrared light and the probe light beam can be co-focused to the same spot for overlapping to increase the efficiency.

Different modulation and demodulation schemes may be employed to extract the signal from the collected probe light. In one embodiment, the infrared laser may be modulated at a frequency $f_{IR}$, with $f_{IR}$ twice the SPM probe mechanical oscillation frequency $f_O$ to synchronize the infrared light beam and the SPM probe mechanical oscillation. By adjusting the timing of the incoming light to the SPM probe oscillation, one IR pulse hits the sample when the tip is on the sample, and the next IR pulse hits the sample when the tip is off the sample. The collected probe light in these two cases is different due to the change of temperature and local sample refractive index with and without IR. By subtracting the probe light signal when the tip is off the surface from the signal when the tip is on the surface, a final signal proportional to local infrared absorption property can be obtained.

In another embodiment, one can also pick $f_{IR}$ to be a harmonic of $f_O$ (i.e., $m \times f_O$ with m an integer). For m>2, multiple IR pulses hit the sample at different times within one SPM probe oscillation cycle. By analyzing the collected probe light amplitude versus the tip-sample distance dependence, one can extract the final signal. More complicated sampling methods with $f_{IR}$ not being a multiple times of $f_O$ have been demonstrated.

Demodulation can also be performed at sideband frequencies that combine the IR laser modulation frequency $f_{IR}$ with the frequency of a secondary modulation, for example the oscillation of the SPM tip at a frequency $f_O$. The collected probe light in such a case is demodulated at a frequency $n \times f_O + m \times f_{IR}$, with n and m integer.

The infrared light source can be pulsed or modulated. For example a controller may generate trigger or sync pulses that command the light source to pulse at a specified rate. Alternately, the light source may pulse based on internal timing and send a sync pulse back to a controller. Alternately, the light source may have an external modulator that periodically modulates its intensity. In one embodiment the light source is modulated or pulsed at frequencies in excess of 10 kHz, 100 kHz, or 1 MHz. Modulating the infrared light at high frequencies reduces the effective thermal diffusion length which could otherwise compromise the spatial resolution of this technique.

The detected probe light is then analyzed by a controller and/or external signal conditioning/demodulating electronics. In one embodiment the detector signal is analyzed by a lock-in amplifier or equivalent device to measure an amplitude of the probe light modulation at the modulation frequency $f_{IR}$ of the laser light source or a harmonic frequency thereof $n \times f_{IR}$ where n is an integer. By using phase sensitive detection such as a lock-in amplifier it is possible to measure only the impact of the infrared light that is absorbed by the sample and causes a periodic deviation of the amplitude of probe light resulting from the sample heating. By measuring the amplitude of the probe light modulation at plurality of locations on the sample, it is possible to make an image of the infrared response of the sample. An aspect of this arrangement is that the infrared properties of the sample can be measured on a scale below the diffraction limit of the infrared light source that illuminates the sample. Instead, the spatial resolution is limited only by the spatial resolution of the scanning near-field optical microscope.

In one embodiment, a tunable can be used as an infrared light source. By fast sweeping wavelengths of the output infrared light, an infrared spectrum can be obtained.

In the case of a narrowband source, e.g. a source with a spectral linewidth of typically <10cm$^{-1}$ and possibly <1 cm$^-$it is possible to create a spectrum directly by measuring the probe light modulation as a function of the emission wavelength (or equivalently wavenumber) of the infrared source. In the case of a broadband source (typical linewidth >100 cm$^{-1}$), it may be desirable to use Fourier transform techniques to extract the wavelength dependence of the amplitude modulation of the probe light and thus extract spectrum. In this case the light from IR source is passed through an interferometer comprising a beamsplitter, a fixed mirror, and a moving mirror, before the light is incident on the sample. The moving mirror in the interferometer can be scanned over a range of different positions while monitoring the amplitude modulation of probe light as a signal to create an interferogram. The interferogram can then be Fourier transformed to obtain a spectrum.

The spatially resolved map can be created by holding the focused IR, probe light spots, and the SPM probe stationary, then the sample can be scanned relative to these focused spots, for example with a sample scanner.

In one embodiment the IR source can be a thermal source, for example a globar as conventionally used in Fourier Transform Infrared (FTIR) spectroscopy and microscopy. Alternately small area thermal emitters for example from Axetris or NovalR or other vendors can be employed. In the case of a thermal emitter it is desirable to modulate the temperature of the device or the output IR power. Some commercial small area thermal emitters can be modulated up to the 100 Hz regime. SPM cantilevers with integral resistive heaters can be modulated in the kHz range due to their small active area and small thermal time constant. Thermal emitters have been fabricated that can be modulated at frequencies in the range of 10 kHz. Various external modulators can also be employed, for example photoelastic modulators, high speed choppers, MEMS mirrors, piezoelectrically deformed mirrors and other modulators that can adjust the intensity, angle, and/or focused spot size of an infrared beam.

The probe light source is in general chosen to be a narrow band light source. The reason for this is that at a given temperature, the optical properties of the sample are substantially constant over a narrow wavelength range. Under a theory of operation, the current apparatus uses the probe light beam to sense dependent variations in the reflectivity of the sample region, due to the absorption by the sample region of IR light from the IR light source. While the IR light source is selected to have a large tuning range or a broadband emission such that it can excite the sample over a plurality of wavelengths, the probe light source is generally selected to be at a fixed wavelength, where the optical properties are substantially constant. Then, as the sample heats up due to absorption of IR radiation, the local reflectivity at the probe wavelength can be monitored without concern about wavelength dependent optical property variations across the bandwidth of the probe light source. By probing with a fixed wavelength beam where the optical properties are constant, the current method and apparatus can avoid dispersive contributions that would be present in the analysis of scattered light in the mid-IR, where there are large wavelength dependent variations in the optical properties, specifically both the real and imaginary index of refraction. The current method and apparatus enable the measurement of the IR absorption separately, substantially suppressing effects of the change in the real index of refraction.

In one embodiment the narrowband probe light can be a visible, near-IR or UV laser. Advantageously, the probe light source can be similar or the same to light sources used for Raman spectroscopy and fluorescence imaging. As such, this apparatus can enable simultaneous or sequential measurements of IR absorption spectra and Raman spectra and fluorescence measurements. In this case the probe light from the sample can be collected by a Raman spectrometer for obtaining simultaneous Raman spectrum and Infrared absorption spectrum. In addition, a portion of the collected probe light can also be filtered by at least one fluorescence filter and analyzed to determine a fluorescent response of the sample. Regarding the narrow band light source for simultaneous Raman and/or fluorescence spectroscopy to IR absorption, the center wavelength can be chosen as substantially equal to one of the following: 244 nm, 257 nm, 325 nm, 364 nm, 457 nm, 473 nm, 488 nm, 514 nm, 532 nm, 633 nm, 660 nm, 785 nm, 830 nm, 980 nm, and 1064 nm.

The embodiments described herein are exemplary. Modifications, rearrangements, substitute processes, alternative elements, etc. may be made to these embodiments and still be encompassed within the teachings set forth herein. One or more of the steps, processes, or methods described herein may be carried out by one or more processing and/or digital devices, suitably programmed.

Depending on the embodiment, certain acts, events, or functions of any of the method steps described herein can be performed in a different sequence, can be added, merged, or left out altogether (e.g., not all described acts or events are necessary for the practice of the algorithm). Moreover, in certain embodiments, acts or events can be performed concurrently, rather than sequentially.

The various illustrative logical blocks, optical and SPM control elements, and method steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method for measuring an infrared absorption spectrum of a sample region, the method comprising:
   a. Interacting a tip of a Scanning Probe Microscope with the sample region;
   b. Illuminating the sample region with an infrared beam from an infrared light source;
   c. Illuminating the sample region and the tip with a probe light from a narrow band light source;
   d. Collecting the probe light, wherein the collected probe light is reflected and emanating from the sample region; and
   e. Analyzing the collected probe light to construct a signal indicative of the infrared absorption spectrum of the sample region.

2. The method of claim 1 wherein the bandwidth of the narrow band light source is less than 8 cm$^{-1}$.

3. The method of claim 1 wherein the infrared light source comprises a tunable infrared laser.

4. The method of claim 1 wherein the infrared light source is a broadband source including a globar or a femto-second laser.

5. The method of claim 4 comprising using a Fast Fourier Transform to construct a spectrum from the broadband source.

6. The method of claim 1 wherein the infrared absorption spectrum is measured with a spatial resolution of less than 10 nm.

7. The method of claim 1 wherein the infrared beam illuminates the sample from an oblique angle from above the sample.

8. The method of claim 1 wherein the infrared beam is modulated at a frequency $f_{IR}$, and wherein the analyzing steps comprises demodulating an amplitude of the collected probe light at a frequency $n*f_{IR}$ where n is an integer.

9. The method of claim 8 wherein the demodulation step is performed at multiple integer values of n.

10. The method of claim 1 wherein the interacting step comprises oscillating the tip at a resonance frequency $f_O$ of the probe.

11. The method of claim 10 wherein the collected probe light is demodulated at a frequency $n*f_O$ where n is an integer.

12. The method of claim 1 wherein at least a portion of the collected probe light is sent to a Raman spectrometer.

13. The method of claim 12 wherein probe light collected by the Raman spectrometer is used to perform tip enhanced Raman spectroscopy at the same sample region as the infrared absorption spectrum.

14. The method of claim 1 wherein the narrow band light source has a center wavelength substantially equal to one of the following: 244 nm, 257 nm, 325 nm, 364 nm, 457 nm, 473 nm, 488 nm, 514 nm, 633 nm, 660 nm, 785 nm, 830 nm, 980 nm, and 1064 nm.

15. A system for measuring an infrared absorption of a sample region, the system comprising a Scanning Probe Microscope (SPM) having a probe tip, an infrared light source, a narrow band probe light source, a probe light collector, and at least one computing device including control, data acquisition, and data analysis elements, the system configured to:

a. Interact the tip with the sample region;
   b. Illuminate the sample region with an infrared beam from the infrared light source;
   c. Illuminate the sample region and the tip with the narrow band probe light beam;
   d. Collect probe light from the sample region with probe light detector; and
   e. Analyze the collected probe light to construct a signal indicative of the infrared absorption spectrum of the sample region.

16. The device of claim 15 further comprising a modulator and a demodulator, further configured to:

a) modulate an intensity of the infrared radiation;
   b) demodulate the collected probe light to determine an amplitude of collected probe light, wherein the amplitude of the collected probe light is used to construct the infrared absorption spectrum of the submicron region of the sample.

17. The system of claim 15 wherein the infrared light source comprises a tunable infrared laser.

18. The device of claim 17 wherein the source of infrared radiation comprises a quantum cascade laser.

19. The device of claim 15 wherein the source of probe light is selected from the group consisting of
   a visible laser, a near-infrared laser, a mid-infrared laser, and an ultraviolet laser.

20. The device of claim 15 wherein the infrared light source comprises a broadband source including a globar or a femto-second laser.

* * * * *